(12) United States Patent
Verhaak

(10) Patent No.: US 8,569,388 B2
(45) Date of Patent: Oct. 29, 2013

(54) PROCESS FOR PREPARING OLEFINS FROM SYNTHESIS GAS USING A COBALT AND MANGANESE CONTAINING CATALYST

(75) Inventor: Michiel Johannes Franciscus Maria Verhaak, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/807,349

(22) PCT Filed: Jun. 23, 2011

(86) PCT No.: PCT/EP2011/060557
§ 371 (c)(1),
(2), (4) Date: Feb. 4, 2013

(87) PCT Pub. No.: WO2012/000883
PCT Pub. Date: Jan. 5, 2012

(65) Prior Publication Data
US 2013/0210941 A1    Aug. 15, 2013

(30) Foreign Application Priority Data
Jun. 30, 2010  (EP) .................................... 10167924

(51) Int. Cl.
*C07C 27/00*  (2006.01)
(52) U.S. Cl.
USPC ........................................ 518/715; 518/700
(58) Field of Classification Search
USPC ................................................ 518/700, 715
See application file for complete search history.

(56) References Cited

U.S. PATENT DOCUMENTS

| 5,502,019 A | 3/1996 | Augustine et al. ............. 502/314 |
| 2002/0010221 A1 | 1/2002 | Ionkina et al. ................. 518/715 |

FOREIGN PATENT DOCUMENTS

| EP | 0359412 | 8/1989 |
| EP | 1681271 | 7/2006 |
| WO | WO9961144 | 12/1999 |
| WO | WO2004103556 | 12/2004 |

OTHER PUBLICATIONS

Mirzaei, A.A. et al.; "Effect of preparation conditions on the catalytic performance of cobalt manganese oxide catalysts for conversion of synthesis gas to light olefins"; Applied Catalysis: A General 306; pp. 98-107; 2006.
Van Der Laan, G.P., et al.: "Kinetics and Selectivity of the Fischer-Tropsch Synthesis: A Literature Review"; Catal. Rev.—Sci. Eng. 41 (3&4) pp. 255-318; 1999.
Weissermel, K., et al.; "Industrial Organic Chemistry—Basic Products of Industrial Synthesis"; 4th Ed. pp. 15-24; 2003.

*Primary Examiner* — Jafar Parsa

(57) ABSTRACT

The invention relates to a process for preparing olefins from synthesis gas, wherein the synthesis gas is contacted with a catalyst which contains cobalt, manganese and a third element selected from the group consisting of aluminium, gallium, indium, thallium, tin, lead and bismuth. Further, the invention relates to a process for preparing such catalyst, and to the catalyst so obtained.

3 Claims, No Drawings

PROCESS FOR PREPARING OLEFINS FROM SYNTHESIS GAS USING A COBALT AND MANGANESE CONTAINING CATALYST

PRIORITY CLAIM

The present application claims priority from PCT/EP2011/060557, filed 23 Jun. 2011, which claims priority from European application 10167924.9, filed 30 Jun. 2010, which is incorporated herein by reference.

The present invention relates to a process for preparing olefins from synthesis gas (syngas) using a catalyst which contains cobalt and manganese.

Syngas is a gas mixture which comprises hydrogen ($H_2$) and carbon monoxide (CO). Syngas may be converted into hydrocarbons by a catalytic process which is usually referred to as the Fischer-Tropsch (FT) process. Catalysts which are commonly used in the FT process, contain iron (Fe), cobalt (Co), nickel (Ni) and/or ruthenium (Ru) as the catalytically active metal. This is for example described by Van der Laan et al. in Catal. Rev.-Sci. Eng., 41, 1999, p. 255 ff.

There is a special interest for the selective and direct production of ethylene, propylene and butylene ($C_2$-$C_4$ olefins) from syngas, which are important chemical hydrocarbon feedstocks. Cobalt-manganese (Co—Mn) catalysts have been shown to have a relatively high selectivity to these olefins. Mirzaei et al. disclose in Applied Catalysis A: General, 306, 2006, p. 98 ff., the preparation of precipitated cobalt manganese catalyst and the use thereof in producing lower olefins from syngas.

An object of the present invention is to find a cobalt and manganese containing catalyst which has good selectivity and/or activity in the preparation of olefins from syngas.

Surprisingly it was found that said object is achieved by adding a third element to the cobalt and manganese containing catalyst, namely an element selected from the group consisting of aluminium (Al), gallium (Ga), indium (In), thallium (Tl), tin (Sn), lead (Pb) and bismuth (Bi).

Accordingly, the present invention relates to a process for preparing olefins from synthesis gas, wherein the synthesis gas is contacted with a catalyst which contains cobalt, manganese and a third element selected from the group consisting of aluminium, gallium, indium, thallium, tin, lead and bismuth.

Preferably, the olefins to be produced in the present process are light olefins, suitably unbranched $C_2$-$C_6$ alkenes, more preferably unbranched $C_2$-$C_4$ alkenes, and most preferably ethylene and propylene.

The catalyst to be used in the present process contains cobalt and manganese. In addition, it contains a third element, namely an element selected from the group consisting of aluminium, gallium, indium, thallium, tin, lead and bismuth.

The atomic ratio of manganese to cobalt in the catalyst to be used in the present process may vary within wide limits. It may be of from 20:1 to 1:20, preferably 10:1 to 1:10, more preferably 10:1 to 1:2, most preferably 8:1 to 1:1.

The amount of the third element in the catalyst to be used in the present process may also vary within wide limits. It may be of from 0.01 to 5 wt. %, preferably 0.05 to 2.5 wt. %, more preferably 0.1 to 2 wt. %, even more preferably 0.2 to 1 wt. %, most preferably 0.3 to 0.8 wt. % based on total amount of the catalyst including any support.

Preferably, the catalyst to be used in the present invention is a supported catalyst. Examples of suitable supports for the present catalyst are titania ($TiO_2$), silica ($SiO_2$), alumina ($Al_2O_3$) and zeolite. A suitable example of such zeolite support is H-mordenite.

The catalyst to be used in the present invention may be prepared in a variety of ways. A supported catalyst may be prepared by means of a process comprising co-precipitation of a manganese salt and a cobalt salt on a support, followed by impregnation with a salt of the third element.

Accordingly, the present invention also relates to a process for preparing a supported catalyst, suitably for use in preparing olefins from synthesis gas, wherein the catalyst contains cobalt, manganese and a third element selected from the group consisting of aluminium, gallium, indium, thallium, tin, lead and bismuth, preferably tin, and is prepared by co-precipitation of a manganese salt and a cobalt salt on a support, followed by impregnation with a salt of the third element.

Preferably, said process for preparing a supported catalyst comprises combining the support with an aqueous solution containing the manganese salt and the cobalt salt, or with an aqueous solution containing the manganese salt and another aqueous solution containing the cobalt salt, resulting in a dispersion, and contacting the dispersion with a basic solution to effect the co-precipitation, and contacting the solid (precipitate) from the dispersion with an impregnating solution containing the salt of the third element.

Said manganese salt may be manganese nitrate. Said cobalt salt may be cobalt nitrate. Preferably, said solution or solutions containing the manganese salt and the cobalt salt is or are heated before combining with the support, for example at 50 to 90° C., preferably 60 to 80° C. The basic solution to be contacted with the dispersion may be a sodium carbonate solution. Preferably, said basic solution is heated before contacting with the dispersion, for example at 50 to 90° C., preferably 60 to 80° C. The amount of base in said solution should be sufficient to allow for co-precipitation of the manganese and cobalt salts on the support. This may be achieved by adding such amount of base that a pH of 8 or greater, preferably a pH of 9 or greater and most preferably a pH of 9.5 or greater is achieved in the dispersion. The solid (precipitate) in the dispersion or slurry resulting from the addition of the basic solution can be removed therefrom by filtration. The separated solid may be washed with water in order to remove substantially all base from the basic solution. Possibly after drying the separated solid, for example at a temperature in the range of from 80 to 120° C., it may further be calcined in the presence of air, at a temperature in the range of from 200 to 800° C., preferably 300 to 700° C., more preferably 400 to 600° C., most preferably 450 to 550° C.

The above-mentioned separated solid is then to be impregnated with the salt of the third element, for example by contacting with an impregnating solution containing the salt of the third element, preferably tin. Said salt of the third element is any soluble salt, such as a nitrate, sulfate, chloride, hydroxide or organic acid salt of said third element. Preferably, said salt of the third element is a nitrate, sulfate, chloride, hydroxide or organic acid salt of tin. Preferred organic acid salts of tin are tin tartrate and tin acetate. The paste that results from contacting the above-mentioned separated solid with an impregnating solution containing the salt of the third element may be heated for example at 40 to 80° C., preferably 50 to 70° C. Possibly after drying the impregnated catalyst, for example at a temperature in the range of from 80 to 120° C., it may further be calcined in the presence of air, at a temperature in the range of from 200 to 800° C., preferably 300 to 700° C., more preferably 400 to 600° C., most preferably 450 to 550° C.

The present invention also relates to a catalyst obtainable by the catalyst preparation process(es) as described above.

Further, the present invention relates to a catalyst which contains cobalt, manganese and a third element selected from the group consisting of aluminium, gallium, indium, thallium, tin, lead and bismuth, preferably tin. Other preferences and embodiments regarding the catalyst from the catalyst preparation process and from the process for preparing olefins from synthesis gas as described above, also apply to said catalyst as such.

Before use in the present process for preparing olefins from synthesis gas, the catalyst may be reduced. Preferably, such pre-reduction is performed by subjecting the catalyst to a gas stream comprising hydrogen and/or carbon monoxide. In addition, said gas stream may comprise nitrogen. The catalyst may for example be pre-reduced at a temperature within the range of from 200 to 700° C., suitably 300 to 600° C., and preferably 400 to 500° C.

The catalyst may be provided to a syngas conversion reactor as a fixed bed, a fluidized bed, or a slurry.

The synthesis gas to be used in the present process for preparing olefins from synthesis gas can be produced by generally known processes, as described for example in Weissermel et al., Industrial Organic Chemistry, Wiley-VCH, Weinheim, 2003, p. 15-24. For example, syngas can be produced by reaction of coal or methane with steam or by reaction of methane with carbon dioxide. Syngas usually has a volume ratio of carbon monoxide to hydrogen of from 3:1 to 1:3. In the present process, preferably a syngas is used which has a volume ratio of carbon monoxide to hydrogen of from 1:0.5 to 1:2.5.

The reaction temperature may be in the range of from 100 to 700° C., suitably 200 to 600° C., and preferably 250 to 500° C., and most preferably 275 to 375° C. The pressure may be of from 1 to 60 bar, preferably of from 10 to 50 bar. The GHSV (gas hourly space velocity) is generally from 100 to 30,000 parts by volume of feed stream per part by volume of catalyst per hour, in $1/(1*hr)$ or $hr^{-1}$.

The invention is further illustrated by the following Examples.

EXAMPLES

Catalyst Preparation

A catalyst containing cobalt and manganese with H-mordenite as support, hereinafter referred to as base-case catalyst, was prepared by means of a co-precipitation procedure.

Manganese nitrate ($Mn(NO_3)_2.6H_2O$) and cobalt nitrate ($Co(NO_3)_2.6H_2O$) were dissolved in demineralized water. The amounts of cobalt nitrate and manganese nitrate were chosen such that the Mn/Co atomic ratio in the final catalyst was 6.

The resulting aqueous solution was heated to 70° C. H-mordenite was then added to the aqueous solution while stirring to obtain a dispersion. The amount of H-mordenite was chosen such that the weight percentage of H-mordenite was 15 wt. %, on the basis of the total weight of cobalt, manganese and H-mordenite.

In a separate vessel, sodium carbonate was dissolved in demineralized water to obtain a 1.0 M (mole/l) solution which was also heated to 70° C. Basic carbonate solution was then added to the dispersion while stirring to achieve a final pH of about 10.

The slurry obtained was left stirring for another 30 minutes and then filtered. The solid residue was washed with warm demineralized water until free of sodium ions, as determined by atomic adsorption analysis. The solids were then dried at 110° C. for 16 hours resulting in a catalyst herein referred to as Reference Catalyst A.

A promoted catalyst was then prepared from the above base-case catalyst, containing cobalt and manganese with H-mordenite as support, by means of an impregnation procedure.

Tin tartrate (tin(II) 2,3-dihydroxybutanedioate) was dissolved in demineralized water. The amount of tin tartrate was chosen such that the weight percentage of tin was 0.5 wt. %, on the basis of the total weight of tin and base-case catalyst. The base-case catalyst was impregnated with the tin tartrate solution resulting in a thick paste. The paste was heated to 60° C. in an oven and regularly stirred to homogenize the paste and finally it was left to dry for 16 hours. The dried material was calcined at 500° C. in air (heating rate 2° C./minute), resulting in a catalyst herein referred to as Catalyst B.

Use of Catalysts in Syngas Conversion

The above Reference Catalyst A (unpromoted) and Catalyst B (promoted with 0.5 wt. % of Sn) were then evaluated in the conversion of syngas in a small-scale, continuous flow, fixed bed setup. Prior to exposure to syngas, these catalysts were reduced in a flow of 50 vol. % hydrogen in nitrogen for 5 hours at a pre-reducing temperature of 350° C. (Reference Catalyst A1 and Catalyst B1) or 450° C. (Reference Catalyst A2 and Catalyst B2).

The catalyst was then cooled down, in the presence of said reducing gas, to 300° C. Then the gas stream was switched to a stream of a mixture of carbon monoxide and hydrogen diluted in nitrogen. The overall gas composition of the latter stream was 33:17:50 (in vol. %) for $CO:H_2:N_2$ ($H_2/CO$ volume ratio was 0.5). The system was pressurized to 15 bar gauge (barg). The pressure and temperature during the reaction were maintained at 15 barg and 300° C., respectively. The gas hourly space velocity (GHSV) was 1,000 $hr^{-1}$.

The product gas stream was analyzed with a gas chromatograph (GC) equipped with a flame ionization detector (FID) and a thermal conductivity detector (TCD). Table 1 shows the CO conversion (indicated as "CO") and the selectivities to carbon dioxide (indicated as "$CO_2$") and to the various hydrocarbon products (indicated by the molecular formula of the hydrocarbon product in question) as obtained in syngas conversions using Reference Catalysts A1 and A2 and Catalysts B1 and B2, at about 70 hours after the introduction of the syngas stream.

CO conversion is herein defined as:

((moles $CO_{in}$–moles $CO_{out}$)/moles $CO_{in}$)*100%

Selectivity to $CO_2$ is herein defined as:

(moles $CO_2$)/(moles converted CO)*100%

Selectivity to hydrocarbon product "x" is herein defined as:

((weight product "x")/total weight of all hydrocarbon products excluding carbon dioxide)*100%

TABLE 1

| Catalyst | CO | $CO_2$ | $CH_4$ | $C_2H_4$ olefin | $C_2H_6$ | $C_3H_6$ olefin | $C_3H_8$ | $C_4H_8$ olefin | $C_4H_{10}$ | $C_{5+}$ | Total $C_2$-$C_4$ olefins |
|---|---|---|---|---|---|---|---|---|---|---|---|
| A1 | 49.1 | 47.8 | 13.7 | 13.5 | 2.4 | 23.5 | 0.8 | 13.8 | 0.5 | 31.8 | 50.8 |
| B1 | 25.5 | 49.9 | 13.8 | 13.1 | 1.8 | 27.4 | 1.2 | 13.6 | 0.8 | 28.3 | 54.1 |
| A2 | 48.6 | 46.9 | 13.4 | 14.1 | 2.5 | 25.9 | 0.9 | 15.3 | 0.6 | 27.3 | 55.3 |
| B2 | 21.8 | 50.5 | 11.7 | 11.0 | 1.6 | 34.0 | 1.3 | 16.9 | 0.8 | 22.7 | 61.9 |

Upon comparing the results from Table 1 between the A1 and B1 catalysts (pre-reduction temperature of 350° C.) and between the A2 and B2 catalysts (pre-reduction temperature of 450° C.), respectively, it appears that the total selectivity to $C_2$-$C_4$ olefins, and in particular the selectivity to propylene ($C_3H_6$), increases significantly because of the presence of tin in the B catalysts.

Further, upon comparing the results from Table 1 between the A1 and B2 catalysts, it appears that the total selectivity to $C_2$-$C_4$ olefins, and in particular the selectivity to propylene ($C_3H_6$), increases even more significantly because of the presence of tin in the B2 catalyst in combination with the higher pre-reduction temperature for the B2 catalyst.

What is claimed is:

1. Process for preparing olefins from synthesis gas, wherein the synthesis gas is contacted with a catalyst which contains cobalt, manganese and a third element selected from the group consisting of aluminium, gallium, indium, thallium, tin, lead and bismuth.

2. Process according to claim 1, wherein the catalyst contains cobalt, manganese and tin.

3. Process according to claim 1, wherein the catalyst is pre-reduced at a temperature within the range of from 400 to 500° C.

* * * * *